(12) United States Patent
Cappola et al.

(10) Patent No.: US 8,460,704 B2
(45) Date of Patent: Jun. 11, 2013

(54) EXTENDED RELEASE FORMULATION OF NEVIRAPINE

(75) Inventors: Michael L. Cappola, Malvern, PA (US); Svetlana Sienkiewicz, New Milford, CT (US); Glenn Charles Snow, Sandy Hook, CT (US); Feng-Jing Chen, Danbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 281 days.

(21) Appl. No.: 12/523,226

(22) PCT Filed: Jun. 4, 2008

(86) PCT No.: PCT/US2008/065705
§ 371 (c)(1), (2), (4) Date: Sep. 17, 2009

(87) PCT Pub. No.: WO2008/154234
PCT Pub. Date: Dec. 18, 2008

(65) Prior Publication Data
US 2010/0278918 A1    Nov. 4, 2010

Related U.S. Application Data

(60) Provisional application No. 60/942,765, filed on Jun. 8, 2007.

(51) Int. Cl.
| A61K 9/22 | (2006.01) |
| A61K 9/00 | (2006.01) |
| A61K 9/14 | (2006.01) |
| A61K 9/28 | (2006.01) |
| A61K 31/00 | (2006.01) |
| C07D 223/10 | (2006.01) |
| C07D 243/10 | (2006.01) |
| A01N 43/00 | (2006.01) |

(52) U.S. Cl.
USPC ........... 424/468; 424/464; 424/465; 424/474; 424/488; 514/211.01; 514/211.03; 514/211.04; 540/484; 540/485; 540/492; 540/495

(58) Field of Classification Search
USPC .......... 424/468, 464, 465, 474, 488; 540/484, 540/485, 492, 495; 514/211.01, 211.03, 211.04
See application file for complete search history.

(56) References Cited

U.S. PATENT DOCUMENTS

| 5,133,974 A | 7/1992 | Paradissis et al. |
| 5,366,972 A | 11/1994 | Hargrave et al. |
| 6,210,712 B1 | 4/2001 | Edgren et al. |
| 2002/0006439 A1* | 1/2002 | Skluzacek et al. ............ 424/464 |
| 2002/0068085 A1 | 6/2002 | Rudnic et al. |
| 2009/0220611 A1 | 9/2009 | Dargelas et al. |

FOREIGN PATENT DOCUMENTS

| EP | 0429987 A2 | 5/1991 |
| WO | 0035419 A2 | 6/2000 |

(Continued)

OTHER PUBLICATIONS van Heewijk et al., "Steady-state pharmacokinetics of nevirapine during once daily and twice daily dosing in HIV-1-infected individuals," 2000; AIDS 14: F77-F82.*

(Continued)

*Primary Examiner* — Jane C Oswecki
(74) *Attorney, Agent, or Firm* — Michael P. Morris; Alan R. Stempel (57) ABSTRACT

The invention relates to an extended release pharmaceutical composition comprising nevirapine.

1 Claim, 4 Drawing Sheets

- Plasma nevirapine concentration-time profile following a single 400 mg dose extended release tablet administration in normal subjects

FOREIGN PATENT DOCUMENTS

| | | | |
|---|---|---|---|
| WO | 0141742 | A2 | 6/2001 |
| WO | 0292095 | A1 | 11/2002 |
| WO | 03022252 | A2 | 3/2003 |
| WO | 2004043435 | A2 | 5/2004 |
| WO | 2004112724 | A2 | 12/2004 |
| WO | 2005048978 | A2 | 6/2005 |
| WO | 2005051234 | A2 | 6/2005 |
| WO | 2007000779 | A2 | 1/2007 |
| WO | 2007036671 | A2 | 4/2007 |
| WO | 2007047371 | A2 | 4/2007 |
| WO | 2007052289 | A2 | 5/2007 |
| WO | 2008154234 | | 12/2008 |

OTHER PUBLICATIONS

Rekhi et al., "Identification of Critical Formulation and Processing Variables for Metoprolol Tartrate Extended-Release (ER) Matrix Tablets," 1999, Journal of Controlled Release; 59(3): 327-342.*

Search Report and Written Opinion of the Australian Patent Office for Singapore Patent Application No. SG 200904846-3, (2009).

Kranz, H et al. "Development of a Single Unit Extended Release Formulation for ZK 81 1 752, a Weakly Basic Drug". European Journal of Pharmaceutical Sciences 26(1): 47-53.2005.

Rekhi, G et al. "Identification of Critical Formulation and Processing Variables for Metoprolol Tartrate Extended-Release (ER) Matrix Tablets". Journal of Controlled Release 59(3): 327-342. 1999.

Lange et al., "Efficacy and durability of nevirapine in antiretoviral drug naive patients" Journal of Acquired Immune Deficiency Syndromes, vol. 34 (1), pp. 40-52, 2003.

PCT/US2008/065705 International Preliminary Report on Patentability, (Dec. 11, 2009).

* cited by examiner

FIGURE 1 - Plasma nevirapine concentration-time profile following a single 400 mg dose extended release tablet administration in normal subjects FIGURE 2 - Plasma nevirapine concentration-time profile following a single 300 mg dose FIGURE 3 - Plasma nevirapine steady state concentration-time profile following a 400 mg dose extended release tablet administration in HIV infected patients Treatment A= Formulation of Ex. 1B, Treatment B = Formulation of Ex.1A

EXTENDED RELEASE FORMULATION OF NEVIRAPINE

BACKGROUND OF THE INVENTION (1) Field of the Invention

The invention relates to a pharmaceutical composition comprising nevirapine.

(2) Description of the Related Art

Nevirapine, or 11-cyclopropyl-5,11-dihydro-4-methyl-6H-dipyrido[3,2-b:2',3'-e][1,4]diazepin-6-one, is a known agent for the treatment of infection by HIV-1 (human immunodeficiency virus, type 1), which acts through specific inhibition of HIV-1 reverse transcriptase. Its synthesis and use are described in various publications including, inter alia, U.S. Pat. No. 5,366,972 and European Patent 0429987B1. Viramune® tablets, a drug product comprising nevirapine, has been approved, in many countries, for use in the treatment of HIV-1 infection.

The currently marketed Viramune® tablets is an immediate release (IR) formulation that is intended to be administered twice daily in order to maintain a therapeutically appropriate blood level of the active ingredient, nevirapine. For the convenience of patients, and to help ensure proper dosing compliance, there has been a longstanding, unmet need for an orally administered, extended release (XR) formulation of nevirapine that could be administered only once per day, while still maintaining a therapeutically appropriate blood level of the active ingredient.

Those having skill in the pharmaceutical art and familiarity with nevirapine will appreciate that nevirapine possesses physicochemical properties that would call into question the feasibility of an XR formulation. More particularly, it will be appreciated that XR formulations are generally designed to be gradually absorbed during transit through the intestines, where the pH is high. Nevirapine is a weak base, and it accordingly can be expected to exhibit low solubility in the intestines. (Nevirapine is a Class II drug substance according to the Biopharmaceutics Classification System.) For this reason, it is reasonable to expect that an XR formulation of nevirapine might transit the GI tract and be excreted without sufficient dissolution and absorption of the nevirapine. This would make an XR formulation unworkable.

Nevirapine has at least one other liability that makes the development of an XR formulation unusually challenging: To be safe, tolerable and effective, the plasma level must never be allowed to fall below the threshhold at which viral replication is inhibited and it must never rise to the level at which there is toxicity or intolerance. For nevirapine, the band between the two is relatively narrow. This means that Cmax,ss/Cmin,ss must be quite flat. Safety/tolerability and efficacy of the immediate release formulation have previously been established while showing a fairly "flat" PK profile observed under steady state conditions after twice daily administration (Cmax,ss/Cmin,ss=1.8 approx). Any extended release (XR) formulation would have to exhibit a peak/trough ratio that is equal to or even less than that of the IR formulation administered twice daily, despite once daily administration of the XR. Otherwise, with a larger peak/trough ratio than observed with IR, the XR formulation would likely be inferior in its clinical risk/benefit profile.

With these rather significant challenges in mind, it is the object of the present invention to provide an orally administered XR formulation of nevirapine.

SUMMARY OF THE INVENTION

The present invention is an extended release (XR) formulation of nevirapine that is suitable for administration only once per day, while still maintaining a therapeutically appropriate blood level of the active ingredient.

DETAILED DESCRIPTION OF THE INVENTION

In its broadest aspect, the extended release formulation provided by the invention exhibits, after administration of a single dose in fasted state to a healthy volunteer, a distinctive pharmacokinetic profile that is characterized by the following two parameters for a dosage form comprising 300 mg of nevirapine:

(a) a geometric mean $C_{max}$ of 1,000 to 2,300 ng/mL; and
(b) a geometric mean $AUC_{0-\infty}$ of 73,400 to 178,100 ng·h/mL); and by the following two parameters for a dosage form comprising 400 mg of nevirapine:

(a) a geometric mean $C_{max}$ of 1,210 to 2,740 ng/mL; and
(b) a geometric mean $AUC_{0-\infty}$ of 109,000 to 237,000 ng·h/mL).

The extended release formulation provided by the invention is further characterized by a geometric mean $T_{max}$ of 10 to 48 hr (again, after single dose administration in fasted state).

The extended release formulation provided by the invention is additionally characterized by the following PK parameters observed after repeated once-daily dosing under steady state conditions:

For a 300 mg dose:
(a) a geometric mean $C_{max,ss}$ of 2,300 to 3,700 ng/mL; and
(b) a geometric mean $AUC_{0-24h,ss}$ of 45,000 to 75,000 ng·h/mL; and For a 400 mg dose:
(a) a geometric mean $C_{max,ss}$ of 3,100 to 4,900 ng/mL; and
(b) a geometric mean $AUC_{0-24h,ss}$ of 60,000 to 99,000 ng·h/mL.

The above noted multiple-dose PK parameters are measured while fasting, during a 24 hour interval after plasma levels of the drug have reached steady state conditions.

The extended release formulation provided by the invention is further characterized by exhibiting a very narrow ratio of $C_{max,ss}/C_{min,ss}$ which is in the range of 1.1 to 2, for both the 300 and 400 mg doses, with said parameter being measured during steady state.

It should be noted that these PK parameters are to be obtained from observed data and not modeled data.

Still further, the extended release formulation of the invention is characterized by having an in vitro dissolution profile such that at least 2% w/w and no more than 30% w/w of the nevirapine is released at 2 hours; at least 20% w/w and up to 100% w/w of the nevirapine is released at 8 hours; at least 40% w/w and up to 100% w/w of the nevirapine is released at 14 hours, when dissolution is measured by the USP Paddle Method at 50 rpm at a volume of 900 mL aqueous buffer containing 6% w/w of sodium lauryl sulfate, having a pH of 6.8 at 37° C.

In preferred embodiments, the extended release formulation of the invention is characterized by having an in vitro dissolution profile such that at least 5% w/w and no more than 20% w/w of the nevirapine is released at 2 hours; at least 30% w/w and no more than 80% w/w of the nevirapine is released at 8 hours; at least 50% w/w and up to 100% w/w of the nevirapine is released at 14 hours, when dissolution is measured by the USP Paddle Method at 50 rpm at a volume of 900 mL aqueous buffer containing 6% w/w of sodium lauryl sulfate, having a pH of 6.8 at 37° C.

In more preferred embodiments, the extended release formulation of the invention is characterized by having an in vitro dissolution profile such that at least 8% w/w and no more than 15% w/w of the nevirapine is released at 2 hours; at least 45% w/w and no more than 60% w/w of the nevirapine is released at 8 hours; at least 75% w/w and no more than 95% w/w of the nevirapine is released at 14 hours, when dissolution is measured by the USP Paddle Method at 50 rpm at a volume of 900 mL aqueous buffer containing 6% w/w of sodium lauryl sulfate, having a pH of between 6.8 at 37° C.

The pharmaceutical composition of the invention may be formulated by combining nevirapine with conventional carriers or excipients. Preferred embodiments of the invention are tablets.

Also preferred are embodiments of the invention that comprise an extended release matrix which comprises a hydrophilic polymer which imparts controlled release of the nevirapine. The hydrophilic polymer can be, but is not limited to hydroxypropylmethylcellulose (HPMC, also known as hypromellose), hydroxypropylcellulose (HPC), hydroxyethylcellulose (HEC), xanthan gum, sodium alginate, polyethylene oxide, and crosslinked homopolymers and copolymers of acrylic acid. Mixtures of the foregoing hydrophilic polymers may also be used. The preferred hydrophilic polymer is HPMC (hypromellose), especially hypromellose 2910 USP, hypromellose 2906 USP or hypromellose 2208 USP, or a mixture thereof.

The formulation provided by the invention can optionally also include other conventional excipients such as fillers, diluents, glidents and binders.

The formulation provided by the invention can be prepared by mixing the individual components (nevirapine drug substance, hydrophilic polymer(s) and optional filler(s), diluent(s), glidant(s) and binder(s)) and then granulating with a granulation solution until complete. The granulation is then dried. The dried granulation is milled, combined with lubricant and mixed to prepare the final blend for compression into tablets. Tablets are compressed by a force of about 10-25 kN, preferably 11-19 kN, and more preferably 13-17 kN into desirable sizes and shapes of hardness from about 11-26 kP, preferably 16-21 kP.

Formulations comprising an extended release matrix comprising between about 20% and 25% by weight of hypromellose are preferred.

More preferred are formulations comprising Hypromellose 2208 (Methocel™ K4M Premium CR).

Particularly preferred is a pharmaceutical tablet wherein each tablet comprises:
(a) 400 mg of anhydrous nevirapine;
(b) 270 mg of Hypromellose 2208 (Methocel™ K4M Premium CR);
(c) 400 mg of lactose monohydrate; and
(d) 10 mg of Magnesium stearate;

wherein each tablet is compressed by a force of about 10-25 kN.

The invention can be further understood by way of the following non-limiting examples, which describe specific tablet formulations.

EXAMPLE 1

400 mg Strength Nevirapine XR Tablet

| Ingredients | Ex. 1A HPMC 20% | Ex. 1B HPMC 25% | Ex. 1C HPMC 30% | Ex. 1D HPMC 40% |
|---|---|---|---|---|
| Nevirapine, anhydrous | 400.00 mg | 400.000 mg | 400.000 mg | 400.000 mg |
| Lactose monohydrate, NF | 400.00 mg | 400.000 mg | 400.000 mg | 400.000 mg |
| Hypromellose 2208 (Methocel™ K4M Premium CR) | 202.50 mg | 270.000 mg | 347.14 mg | 540.000 mg |
| Magnesium stearate (vegetable grade) | 10.00 mg | 10.000 mg | 10.000 mg | 10.000 mg |
| Tablet weight | 1012.50 mg | 1080.00 mg | 1157.14 mg | 1350 mg |

Processing Method

The lactose, nevirapine drug substance and hypromellose are mixed and then granulated with water until complete. The granulation is then dried. The dried granulation is milled, combined with lubricant (magnesium stearate) and mixed to prepare the final blend for compression into tablets. Tablets are compressed by a force of about 10-25 kN into 9.3×19.0 mm tablets.

EXAMPLE 2

300 mg Strength Nevirapine XR Tablet

| Ingredients | Ex. 2A HPMC 20% | Ex. 2B HPMC 25% | Ex. 2C HPMC 30% | Ex. 2D HPMC 40% |
|---|---|---|---|---|
| Nevirapine, anhydrous | 300.000 mg | 300.000 mg | 300.000 mg | 300.000 mg |
| Lactose monohydrate (Granulac 200) | 300.000 mg | 300.000 mg | 300.000 mg | 300.000 mg |
| Hypromellose 2208 (Methocel™ K4M Premium CR) | 151.875 mg | 202.500 mg | 260.355 mg | 405 mg |
| Magnesium stearate (vegetable grade) | 7.50 mg | 7.500 mg | 7.50 mg | 7.500 mg |
| Tablet weight | 759.375 mg | 810.000 mg | 867.855 mg | 1012.5 mg |

Processing Method

The lactose, nevirapine drug substance and hypromellose are mixed and then granulated with water until complete. The granulation is then dried. The dried granulation is milled, combined with lubricant (magnesium stearate) and mixed to prepare the final blend for compression into tablets. Tablets are compressed by a force of about 10-25 kN into 9.3×19.0 mm tablets.

EXAMPLE 3

400 mg Strength Nevirapine XR Tablet

| Ingredients | Ex. 3A HPMC 20% | Ex. 3B HPMC 25% |
|---|---|---|
| Nevirapine, anhydrous | 400.000 mg | 400.000 mg |
| Lactose monohydrate (Granulac 200) | 400.000 mg | 400.000 mg |
| Hypromellose 2910 (Methocel ™ E4M Premium CR) | 202.5 mg | 270 mg |
| Magnesium stearate (vegetable grade) | 10 mg | 10 mg |
| Tablet weight | 1012.5 mg | 1080 mg |

Processing Method

The lactose, nevirapine drug substance and hypromellose are mixed and then granulated with water until complete. The granulation is then dried. The dried granulation is milled, combined with lubricant (magnesium stearate) and mixed to prepare the final blend for compression into tablets. Tablets are compressed into 9.3×19.0 mm tablets.

EXAMPLE 4

300 mg Strength Nevirapine XR Tablet

| Ingredients | Ex. 4A HPMC 20% | Ex. 4B HPMC 25% |
|---|---|---|
| Nevirapine, anhydrous | 300.000 mg | 300.000 mg |
| Lactose monohydrate (Granulac 200) | 300.000 mg | 300.000 mg |
| Hypromellose 2910 (Methocel ™ E4M Premium CR) | 151.875 mg | 202.500 mg |
| Magnesium stearate (vegetable grade) | 7.50 mg | 7.500 mg |
| Tablet weight | 759.375 mg | 810.000 mg |

Processing Method

The lactose, nevirapine drug substance and hypromellose are mixed and then granulated with water until complete. The granulation is then dried. The dried granulation is milled, combined with lubricant (magnesium stearate) and mixed to prepare the final blend for compression into tablets. Tablets are compressed by a force of about 10-25 kN into 9.3×19.0 mm tablets.

The pharmacokinetic parameters of the formulations described above were assessed in a healthy subject population of N=17 following a single dose administration. A summary of the results appears in Table 1, below.

TABLE 1

Summary of single dose pharmacokinetic parameters [geometric mean (% geometric CV)] for Nevirapine Formulations in normal subjects (N = 17)

| Formulation | $AUC_{0-\infty}$ (ng · h/mL) | $C_{max}$ (ng/mL) | $t_{max}$ (h) |
|---|---|---|---|
| 400 mg Nevirapine, HPMC 20% E | 182,000 (31%) | 1,990 (28%) | 30.4 (31%) |
| 400 mg Nevirapine, HPMC 20% K | 149,000 (32%) | 1,990 (27%) | 23.5 (18%) |
| 400 mg Nevirapine, HPMC 25% K | 155,000 (30%) | 1,970 (32%) | 22.7 (44%) |
| 400 mg Nevirapine, HPMC 30% K | 166,000 (28%) | 2,110 (24.3%) | 27.5 (44%) |
| 400 mg Nevirapine, HPMC 40% K | 145,000 (47%) | 1,610 (43%) | 25.7 (43%) |
| 300 mg Nevirapine, HPMC 20% E | 118,000 (31%) | 1,660 (26%) | 24.6 (18%) |
| 300 mg Nevirapine, HPMC 20% K | 137,000 (51%) | 1,660 (42%) | 23.9 (27%) |
| 300 mg Nevirapine, HPMC 25% K | 126,000 (34%) | 1,770 (25%) | 24.5 (29%) |
| 300 mg Nevirapine, HPMC 30% K | 109,000 (29%) | 1,340 (27%) | 24.2 (41%) |
| 300 mg Nevirapine, HPMC 40% K | 97,800 (64%) | 1,350 (44%) | 25.0 (44%) |
| 400 mg Nevirapine, IR | 210,000 (22%) | 3,130 (12%) | 4.31 (117%) |
| 200 mg Nevirapine, IR | 114,000 (30%) | 1,740 (21%) | 2.17 (147%) |

The pharmacokinetic parameters of the formulations described above were also assessed following multiple dose administration (once daily nevirapine XR for 17 days) in a HIV infected patient population previously treated with Viramune® immediate release tablets. A summary of the results appears in Table 2, below.

TABLE 2

Summary of steady state pharmacokinetic parameters for Immediate Release (IR) and 400 mg eXtended Release (XR) tablets in HIV-infected patients

| Treatment | | $t_{max}$ (hr) | $C_{max}$ (ng/mL) | $C_{min}$ (ng/mL) | $AUC_{0-24}$ (hr · ng/mL) |
|---|---|---|---|---|---|
| IR | gMean | 1.8 | 5,576 | 2,976 | 96,137 |
| (N = 19) | gCV % | 130 | 26 | 31 | 26 |
| ER 25% K | gMean | 4.3 | 3,911 | 2,622 | 75,544 |
| (N = 18) | gCV % | 134 | 26 | 35 | 29 |
| XER 20% K | gMean | 5.8 | 3,904 | 2,609 | 79,308 |
| (N = 9) | gCV % | 92 | 37 | 45 | 38 | gMean = geometric mean,
gCV = geometric CV.

TABLE 3

Projected Summary of steady state pharmacokinetic parameters for 300 mg eXtended Release (XR) tablets in HIV-infected patients

| Treatment | | $t_{max}$ (hr) | $C_{max}$ (ng/mL) | $C_{min}$ (ng/mL) | $AUC_{0-24}$ (hr · ng/mL) |
|---|---|---|---|---|---|
| ER 25% K | gMean | 4 | 3,000 | 1,970 | 57,000 |
| ER 20% K | gMean | 5 | 2,930 | 1,960 | 59,500 |

Dissolution

Figure 1:
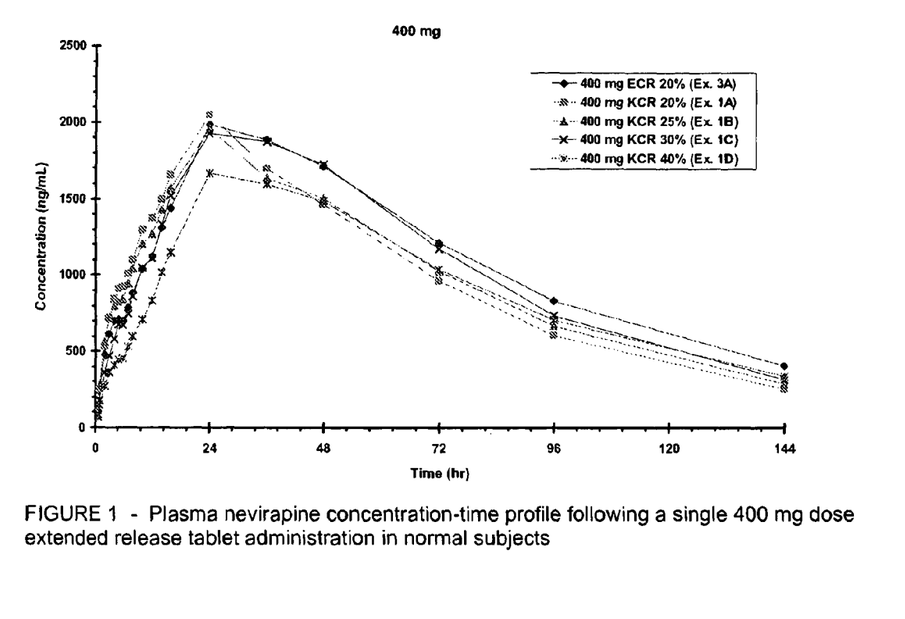
FIGS. 1 and 2, respectively show the concentration of nevirapine in the blood plasma, as a function of time, obtained by the administration to healthy subjects of a single 400 mg or 300 mg tablet extended release dosage form of nevirapine in accordance with the present invention.
Figure 2:
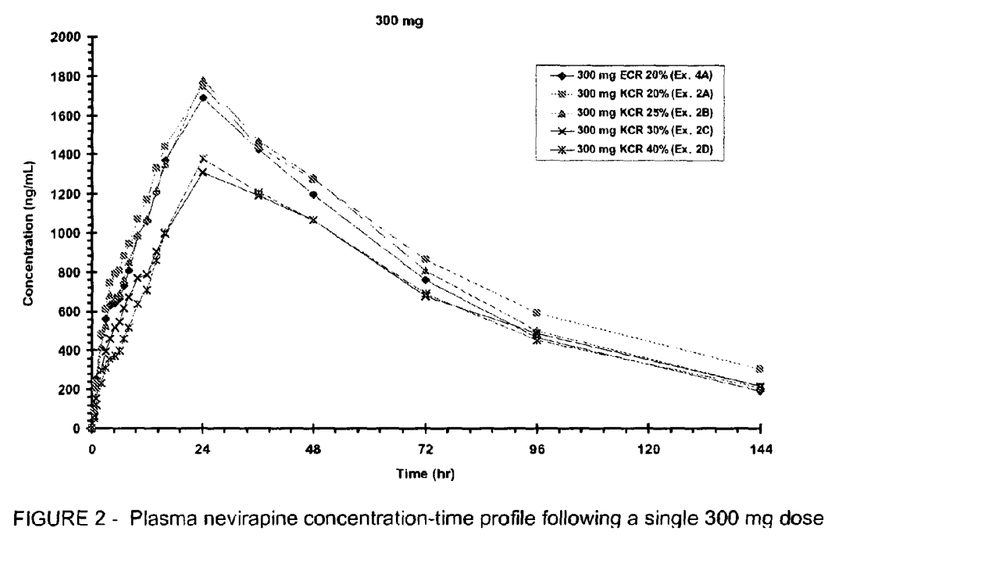
Figure 3:
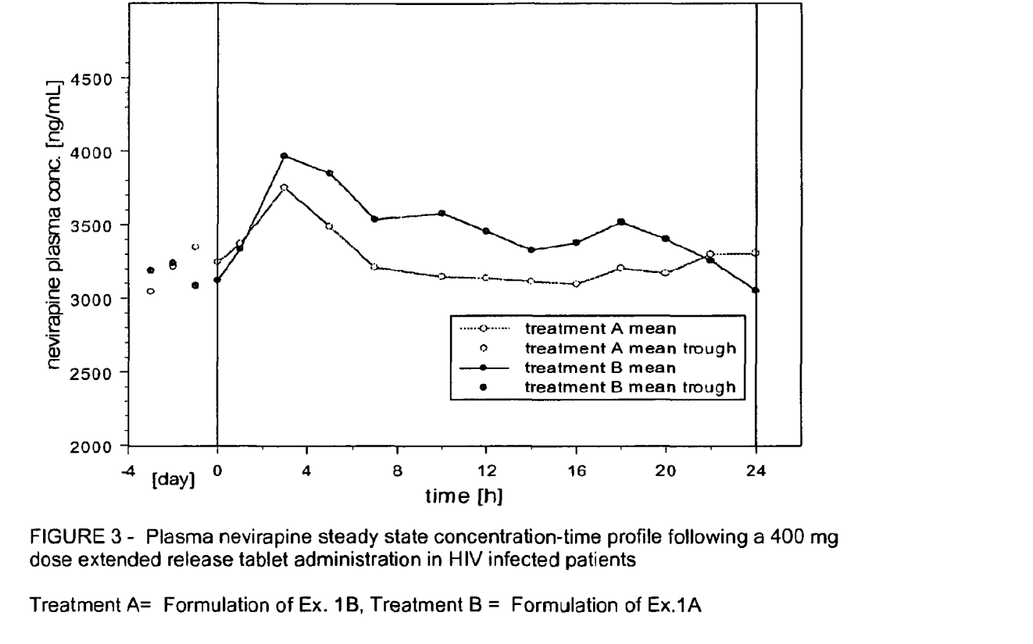
FIG. 3 depicts the steady state concentration of nevirapine in the blood plasma, as a function of time, obtained by repeated once daily administration to healthy subjects of 400 mg tablet extended release dosage forms of nevirapine in accordance with the invention.
Figure 4:
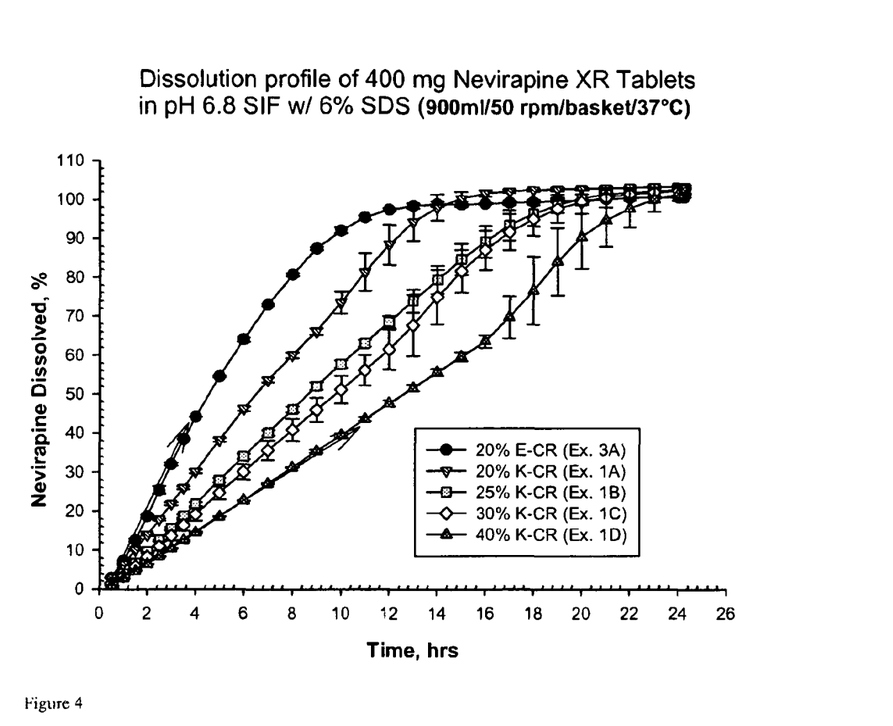
FIG. 4 depicts the dissolution profile of the extended release formulation according to the invention.

The dissolution profiles of the five formulations described by Examples 1, 2, 3 and 4 are depicted by FIG. 4. The dissolution information depicted was obtained by the test method described below.

Dissolution Test Method

The USP paddle method is the paddle method described, e.g., in U.S. Pharmacopoeia XXII (1990).

USP Apparatus I (baskets) at 50 rpm in 900 mL medium at 37° C. Baskets (#10 mesh) were chosen to assure that the tablets would not stick to the bottom of the vessel and thereby minimize surface area available to solution during testing.

Tablet dissolution was performed using a VanKel VK 750 D Heater/Circulator Model 65-3000, VanKel VK 7000 or 7010 Dissolution Testing Station, and VanKel Pump Model 17-2200 (VanKel, Cary, N.C.).

Drug substance dissolution rate was measured using an on-line Cary 50 UV-Visible Spectrophotometer (Varian Australia Pty LTD) at 330 nm against external standards.

The tested dissolution media: 0.05M phosphate buffer ($NaH_2PO_4$/NaOH or $NaH_2PO_4$/$Na_2HPO_4$/NaOH—all EM Science, Darmstadt, Germany) containing 6% Sodium Lauryl Sulfate (13% Sodium Lauryl Sulfate in deionized water, Anachemia Chemicals, Rouses Point, NY or Sodium Lauryl Sulfate, Spectrum Chemical MFG. CORP.) and adjusted to pH 6.8.

Dissolution was performed using 10 mesh stainless steel baskets.

Dissolution parameters:
medium volume: 900 mL
temperature: 37.3° C.
rotation rate: 50 rpm
sampling timepoints: every 30 min. for initial four hours, then every hour (4-24 hours)
infinity spin: 15 minutes at 250 rpm
on line filters: 10 µm full flow filter (VanKel, Cary, N.C. or Quality Lab Accessories L.L.S.).

What is claimed is:

1. A method for treating HIV-1 infection which comprises once daily adminstration to a human infected by HIV-1 a tablet pharmaceutical dosage form wherein each tablet comprises:
    (a) 400 mg of anhydrous nevirapine;
    (b) 270 mg of Hypromellose 2208;
    (c) 400 mg of lactose monohydrate; and
    (d) 10 mg of Magnesium stearate;
wherein each tablet is compressed by a force of 10-25 kN.

* * * * *

UNITED STATES PATENT AND TRADEMARK OFFICE
CERTIFICATE OF CORRECTION

PATENT NO.       : 8,460,704 B2  
APPLICATION NO.  : 12/523226  
DATED            : June 11, 2013  
INVENTOR(S)      : Cappola et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 483 days.

Signed and Sealed this  
Tenth Day of March, 2015

Michelle K. Lee  
*Deputy Director of the United States Patent and Trademark Office*